United States Patent [19]

DeLonzor et al.

[11] Patent Number: 5,678,544
[45] Date of Patent: *Oct. 21, 1997

[54] DISPOSABLE PULSE OXIMETER SENSOR

[75] Inventors: Russell DeLonzor, Union City; Lee Middleman, Portola Valley, both of Calif.

[73] Assignee: Nellcor Puritan Bennett Incorporated, Pleasanton, Calif.

[*] Notice: The term of this patent shall not extend beyond the expiration date of Pat. No. 5,246,003.

[21] Appl. No.: 515,504

[22] Filed: Aug. 15, 1995

Related U.S. Application Data

[63] Continuation of Ser. No. 120,267, Sep. 13, 1993, Pat. No. 5,469,845, which is a continuation-in-part of Ser. No. 838,565, Feb. 19, 1992, Pat. No. 5,246,003, which is a continuation-in-part of Ser. No. 751,405, Aug. 28, 1991, abandoned.

[51] Int. Cl.$^6$ ............................................. A61B 5/00
[52] U.S. Cl. .......................... 128/633; 128/664; 351/41
[58] Field of Search .................... 250/208.1, 214.1, 250/216, 335.11, 341.8, 341.1, 339.12; 128/633, 664–666; 356/41

[56] References Cited

U.S. PATENT DOCUMENTS

| | | | |
|---|---|---|---|
| 3,617,374 | 11/1971 | Hodson et al. | 117/212 |
| 4,621,643 | 11/1986 | New, Jr. et al. | 128/633 |
| 4,644,092 | 2/1987 | Gentry | 174/36 |
| 4,695,719 | 9/1987 | Wilwerding | 250/216 |
| 4,825,879 | 5/1989 | Tan et al. | 128/633 |
| 4,848,335 | 7/1989 | Manes | 128/303.1 |
| 4,865,038 | 9/1989 | Rich et al. | 128/633 |
| 4,928,691 | 5/1990 | Nicolson et al. | 128/633 |
| 4,964,408 | 10/1990 | Hink et al. | 128/633 |
| 5,069,213 | 12/1991 | Polczynski | 128/665 |
| 5,094,240 | 3/1992 | Muz | 128/633 |
| 5,109,849 | 5/1992 | Goodman et al. | 128/633 |
| 5,237,994 | 8/1993 | Goldberger | 128/633 |
| 5,246,003 | 9/1993 | DeLonzor | 128/633 |
| 5,261,415 | 11/1993 | Dussault | 128/719 |

FOREIGN PATENT DOCUMENTS

WO 89/09566  10/1989  WIPO .

*Primary Examiner*—Robert Nasser
*Attorney, Agent, or Firm*—Townsend and Townsend and Crew LLP

[57] ABSTRACT

A conformable sensor which uses a flexible substrate, preferably a polyester strip is disclosed. The emitter and detector are mounted on one portion of the strip with conductive traces connecting to them. The second portion of the strip is folded over to cover the emitter and detector and traces, with openings for the emitter and detector. A conductive coating is applied to the strip to provide shielding from electromagnetic interference. Preferably, a second portion of the strip, which folds over the first portion, also has a Faraday shield covering the opening over the detector. The detector and emitter semiconductor chip die (rather than use encapsulated chips) may be mounted directly on the polyester strip so that it is in contact with one of the conductive traces.

7 Claims, 6 Drawing Sheets

DISPOSABLE PULSE OXIMETER SENSOR

This application is a continuation of U.S. Ser. No. 08/120,267, filed Sep. 13, 1993, now U.S. Pat. No. 5,469,845, which is a continuation-in-part of U.S. Ser. No. 07/838,565, filed Feb. 19, 1992, now U.S. Pat. No. 5,246,003, which is a continuation-in-part of U.S. Ser. No. 07/751,405, filed Aug. 28, 1991 now abandoned.

BACKGROUND

This invention relates to sensors for use with non-invasive pulse monitors such as plethysmographs or pulse oximeters.

A plethysmograph is a pulse monitor. The plethysmograph sensor shines light into the patient's tissue, and the light transmitted through the tissue is received by a photodetector. The photodetector generates electrical signals corresponding to the transmitted light levels and transmits the signals to a monitor for processing. Arterial blood will absorb some of the light, with more light being absorbed when there is more blood. Thus, changes in the amount of transmitted light are related to pulses of arterial blood in the illuminated tissue.

A pulse oximeter is a device for non-invasively determining the oxygen saturation of arterial blood. The pulse oximeter sensor shines light at two different wavelengths (one in the red range, the other in the infrared range) through a portion of the patient's blood-perfused tissue. The red and infrared light transmitted through the tissue is detected by a photodetector. The amount of light absorbed varies with the amount of oxygen in the blood, and varies differently for red and infrared light. The pulse oximeter monitor computes blood oxygen saturation based on the changes in the two detected light levels between two points in time.

There are several types of sensors for plethysmographs and pulse oximeters. One is a surface sensor in which the light emitter and the photodetector are mounted on the same sensor face. The sensor is attached to the patient with both the light emitter and the detector on the same side of the patient's appendage (e.g., on the patient's forehead). This type of sensor detects light reflected back from the tissue, rather than light transmitted through an appendage. The signal detected will thus be weaker in most cases. The sensor is typically attached with a strap, headband or tape over the sensor, or an adhesive pad between the sensor and the skin.

Another type of sensor is a clamp design, such as that described in U.S. Pat. No. 4,685,464. The durable sensor described in that patent has deformable pads creating conforming tissue contacting surfaces to which the emitters and photodetector are secured. The deformable pads are disposed in a hinged rigid housing that clips on the patient like a clothes pin. This relies on a clamping force to secure the sensor to the patient. The force of the sensor against the patient's tissue could reduce the flow of blood to that region. This exsanguination of the tissue beneath the sensor adversely affects pulse detection and analysis by suppressing the pulse in that portion of the tissue. As a result, the sensor site must typically be checked or moved every four hours to insure adequate perfusion. Because of its relatively large mass, however, the clamp design is more susceptible to signal-distorting motion artifact. i.e., differential motion between the sensor and the patient.

A third sensor design is described in U.S. Pat. No. 4,830,014. The conformable sensor described in that patent has emitters and a photodetector mounted in the same side of a flexible web. The web wraps around a portion of the patient's tissue (such as a finger) so that the light from the emitters must travel through the tissue before reaching the detector. The web attaches to the skin with an adhesive surface on the emitter and detector side of the web. Because of its relatively low mass and the adhesive, this sensor adheres closely to the patient's skin and minimizes the effects of motion artifact. In addition, its flexibility and use of adhesive to secure it minimizes the exsanguination caused by rigid sensors. Thus the sensor site typically only needs to be checked every eight hours.

One problem with such a conformable sensor is that of electromagnetic and photic interference with the detector. In the clamp-type of sensor, a Faraday shield, which is a grid of wires, covers the emitter to block out electromagnetic interference. In addition, shielded cabling is used to prevent interference with the conductive lines carrying the signal from the detector. The use of such shielded cabling to connect up to the detector on a conformable sensor makes the sensor bulky and more expensive.

In one type of sensor, disclosed in U.S. Pat. No. 4,621,643, a coding resistor is attached to the probe to indicate the wavelength of light emitted by the particular emitter. The selecting and attaching of such a coding resistor to a conformable sensor makes the manufacturing process difficult and expensive.

It is desirable to have an inexpensive conformable sensor which is easy to manufacture and provides appropriate shielding and a coding resistor.

SUMMARY OF THE INVENTION

The present invention provides a conformable sensor which uses a flexible substrate, preferably a polyester strip. The emitter and detector are mounted on one portion of the strip with conductive traces connecting to them. The second portion of the strip is folded over to cover the emitter and detector and traces, with openings for the emitter and detector. A conductive coating is applied to the strip to provide shielding from electromagnetic interference. In certain embodiments, a second portion of the strip, which folds over the first portion, may also have a Faraday shield covering the opening over the detector.

The Faraday shield is preferably connected to the conductive coating on the first portion of the strip through a conductive via. The conductive coating is in turn connected to the ground trace on the first portion of the strip through another conductive via. The coating is deposited using the same process which produces the conductive traces. This makes the sensor very easy and inexpensive to manufacture, giving a very good disposable sensor.

The present invention also provides a unique mounting method for the detector and emitter semiconductor chips. According to prior art methods, when an encapsulated chip is used, the die is wire bonded to leads in a separate manufacturing step, and the leads are then connected to the traces on the strip. Rather than use encapsulated chips having preattached leads, the die itself may be mounted directly on the polyester strip so that it is in contact with one of the conductive traces. A wire bonding may be done to another of the conductive traces from a face of the die opposite the die face in contact with the conductive trace. The die may be also mounted directly over the substrate opening, rather than being on the opposite side of the opening in the strip, which requires that the die have two contacts on its face confronting the substrate. The die can be covered with a clear epoxy to protect it after it is connected. This epoxy may be used as a lens in one embodiment. After an emitter die is directly mounted as described, it can be tested to determine its emission wavelength and a coding resistor on the substrate can thereafter be trimmed to provide an indication of the wavelength, or alternatively a discrete resistor having an appropriate value can be attached to the substrate.

A unique connector is provided which operates like a belt buckle. One end of the conductive strip having the conductive traces is passed through slots in a plug and then folded back over a central portion and secured. The plug is then forced into a socket which has an opening with pins extending downward to contact the conductive traces. The folded, flexible polyester substrate forms a spring action to press the contacts against the pins.

The present invention also provides a coding resistor which has a value corresponding to the actual wavelength of the particular emitter used. The coding resistor can be a ceramic resistor bonded to traces on the substrate or a laser trimmable resistor which is deposited on the substrate along with the conductive traces. Thus, it can easily be trimmed to the appropriate value during the manufacturing process.

For a fuller understanding of the nature and advantages of the invention, reference should be made to the ensuing detailed description taken in conjunction with the accompanying drawings.

DETAILED DESCRIPTION OF THE PREFERRED EMBODIMENTS

Figure 1:
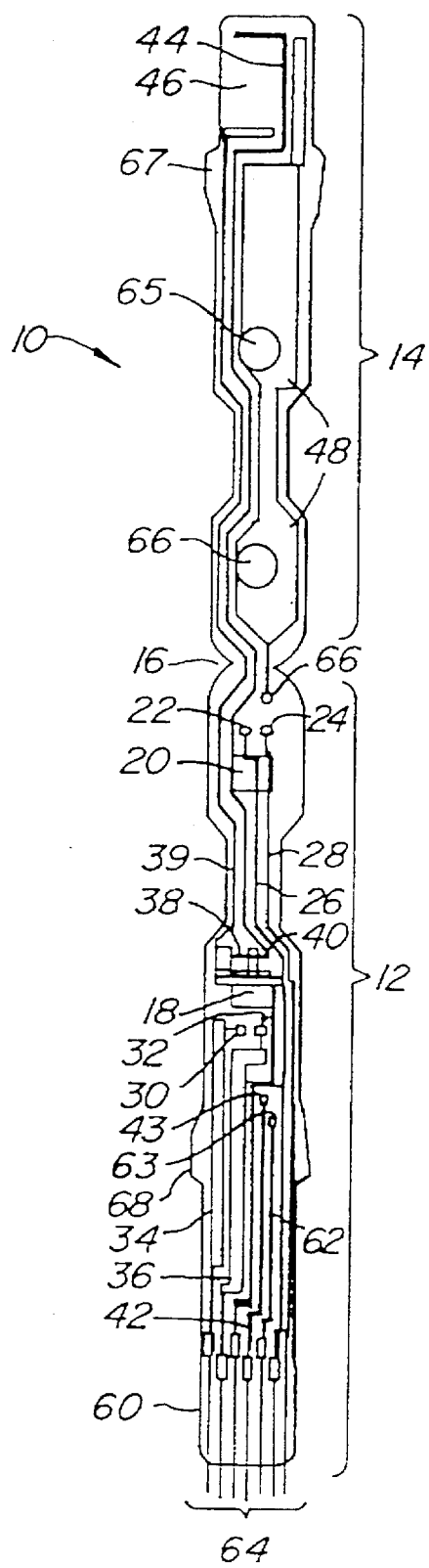
FIG. 1 is a view of the front of the substrate of a sensor according to the preferred embodiment of this invention.
Figure 2:
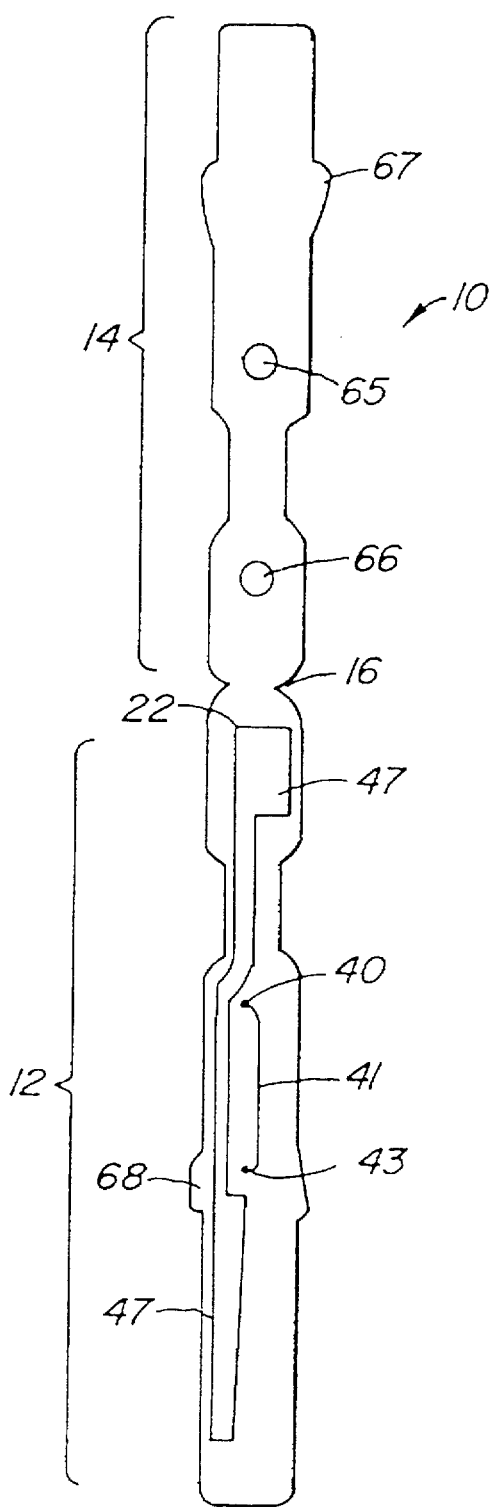
FIG. 2 is a view of the back of the substrate of FIG. 1.

FIG. 1 is an elevational view of the front, and FIG. 2 is an elevational view of the back, of the substrate of a sensor according to the preferred embodiment of this invention. Generally, the electrooptical sensor components described below are deposited or mounted on a polyester substrate tape 10 in a configuration dictated by this invention. Poly-Flex Circuits, Inc., of Cranston, R.I., is the preferred vendor for the substrate and for the conductive trace deposition and component mounting processes.

Polyester substrate 10 has a first portion 12 and a second portion 14 which is folded over portion 12 from a hinge point 16. In the preferred embodiment, polyester substrate 10 is approximately 5 mils thick. In any event, it should be greater than approximately 3 mils to avoid capacitive coupling between the grounded shield and the other traces.

The sensor's photoemitter 18 and photodetector 20 (shown in FIG. 1 as phantom rectangles) are mounted on portion 12 of substrate 10. The leads of photodetector 20 are bonded to conductive traces 26 and 28 at points 22 and 24, respectively, preferably using Poly-Flex Circuits, Inc., Poly-Solder "F" conductive adhesive. The leads of photoemitter 18 are connected to traces 34 and 36 at points 30 and 32, respectively, in the same manner. Epoxy is placed over both sets of leads, and a dielectric coating is applied to the entire circuit.

A coding resistor 38 is connected between trace 39 on the front of substrate portion 12 and, via a conductive through-hole 40, a trace 41 on the back side of substrate portion 12. Trace 41 connects to trace 42 on the front side of substrate portion 12 via through-hole 43. The value of resistor 38 is used to indicate the wavelength of light emitted by photoemitter 18 as discussed in U.S. Pat. No. 4,621,643.

The circuit shown in FIGS. 1 and 2 also contains a feature used in an alternative embodiment. Trace 39 and a trace 44 bound an open area 46 on the front of substrate portion 14. Trace 44 communicates with trace 41 on the back of substrate 10 via through-hole 40. A printed resistor may be formed in area 46 by depositing a somewhat less conductive ink. The value of the printed resistor may be adjusted by making a lateral cut, possibly followed by a longitudinal cut, in the inked area 46. The cut may be made by a laser or by any other suitable cutting means. This printed resistor may be used in place of discrete resistor 38. Other shaped cuts may be used as well.

In yet another alternative embodiment, a discrete transistor may be used in series or in parallel with a printed resistor. A circuit other than the circuit shown in FIG. 1 must be used, of course, to provide the series or parallel resistor relationship.

In order to minimize the effects of ambient electromagnetic noise on the signal generated by the sensor, shielding is provided in particularly sensitive portions of the sensor. Specifically, conductive coating areas 47 and 48 are provided on the back of substrate portion 12 and on the front of substrate portion 14, respectively. The conductive coating is preferably silver ink of the same type used to form the traces for the electrical connections. It should be also noted that if a transparent substrate were used in place of the preferred opaque substrate 10, the conductive coating areas would provide some shielding from the effects of ambient light as well.

Traces 26, 28, 34, 36, 39, and 42 extend to a connector area 60 on the end of the front side of substrate portion 12. A grounding trace 62 also extends from the connector area 60. Grounding trace 62 connects to conductive coating area 47 via conductive through-hole 63, and conductive coating area 47 connects to conductive coating area 48 via a conductive through-hole 66. All traces end in widened contact pads 64 for connection to the sensor's cable, as discussed below.

Figure 3:
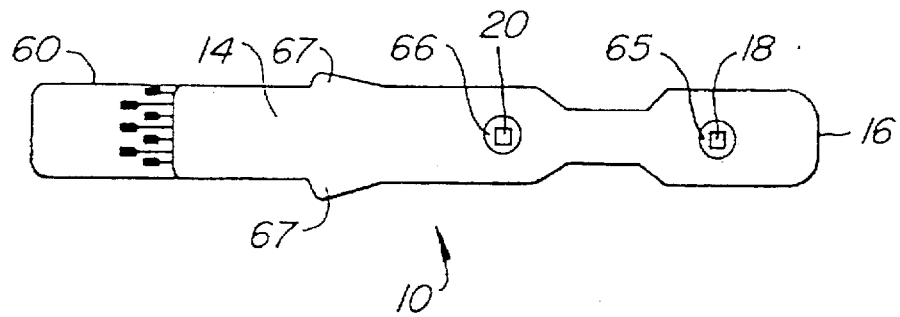
FIG. 3 is a view of a folded substrate according to the preferred embodiment.

After the optical components and coding resistor have been mounted, substrate 10 is folded about hinge 16 so that the fronts of substrate portions 12 and 14 meet. Folding at hinge 16 ensures that holes 65 and 66 will line up with photoemitter 18 and photodetector 20, respectively, as shown in FIG. 3. Folding at hinge 16 also makes tabs 67 on substrate portion 14 line up with tabs 68 on substrate portion 12. In addition, contact pads 64 in connector area 60 remain uncovered when substrate 10 is folded.

Figure 5:
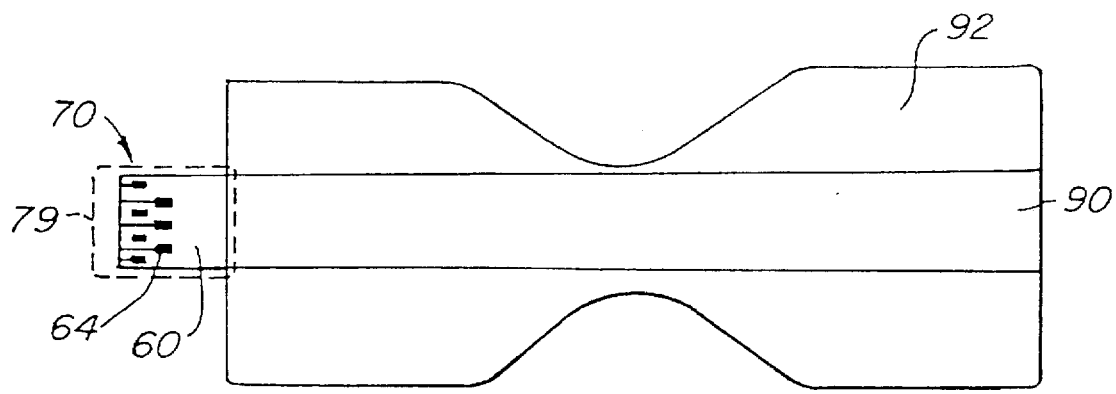
FIG. 5 is a view of the folded substrate inside a bandage.
Figure 4:
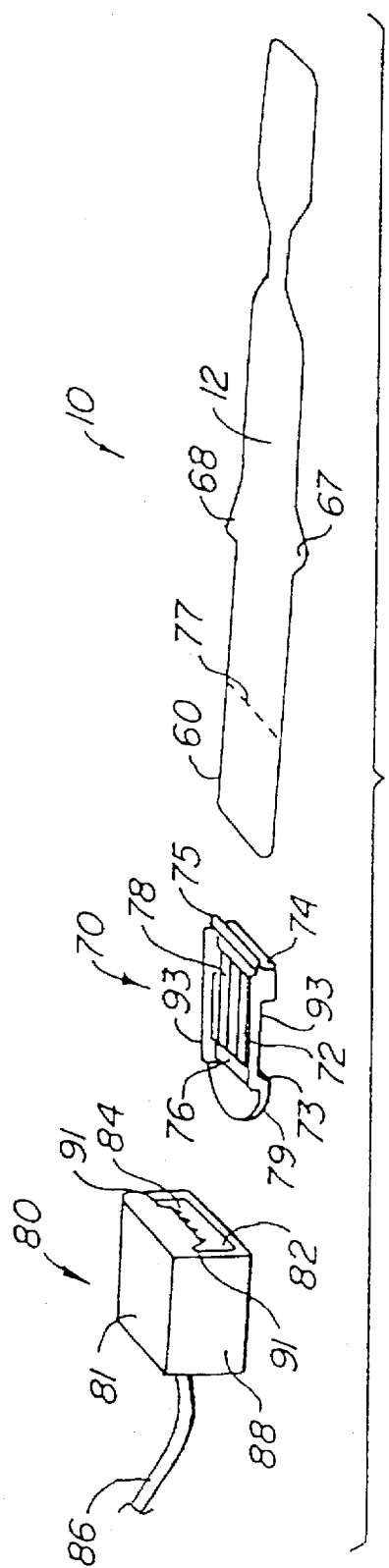
FIG. 4 is an exploded view of the folded substrate, connector plug and cable connector.

A connector plug 70 for attaching to the end of the substrate and a cable connector are shown in FIG. 4. Connector area 60 of substrate 10 is inserted beneath bar 75 into slot 74. Connector area 60 passes through slot 76 and is folded upward and backward about dotted line 77 to pass over central support 72, then passes through back through slot 74. Insertion continues until tabs 67 and 68 meet plug 70. The contact pads 64 are then disposed over central support 72 as shown in FIG. 5.

Connector plug 70 can then be inserted into an opening 82 in a connector 80. As plug is inserted, contact pads 64 (which are now on the top of plug 70) will come into contact with a number of pins 84. Pins 84 communicate with conductors in cable 86, which is connected to the pulse oximeter monitor.

Pins 84 line up with grooves 78 formed on the top of central support 72. As plug 70 is inserted into connector 80, pins 84 press substrate 10 down into grooves 78. The resiliency of the substrate material ensures good electrical contact between contact pads 64 and pins 84. In addition, because of the way the substrate is bent about plug 70, connector area 60 will be bowed upward, providing a spring action due to its resiliency. Thus, when plug 70 in inserted into slot 82, the spring action will force contact pads 64 up against pins.

To ensure that plug 70 is inserted into cable connector 80 in the proper orientation, a pair of grooves 90 are formed in slot 82 that mate with bars 92 on plug 70. In addition, when plug 70 has been inserted all the way into connector 80, the resilient spring action of the folded substrate will force plug 70 downward causing edge 73 of the plug to move downward and catch on the backside of connector 80, holding it in place.

A conductive shield is provided on cable connector face 88, face 89 and the face opposite face 88. This shield communicates with a ground signal in cable 86.

FIG. 5 is a top view of the assembled sensor. After mounting plug 70 on substrate 10, a white polyethylene covering 90 is wrapped about folded substrate 10. A pair of holes in covering 90 line up with holes 65 and 66 on the bottom side of the view shown in FIG. 5 to expose the optical components. The now covered substrate 10 is mounted on a clear, permeable adhesive web 92.

Figure 7:
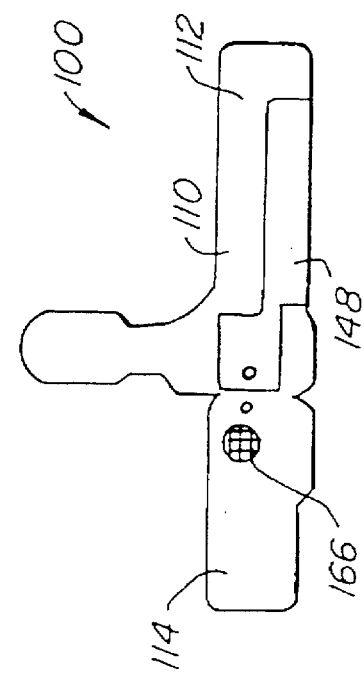
FIG. 7 is a view of the back of the substrate of the sensor of FIG. 6.
Figure 6:
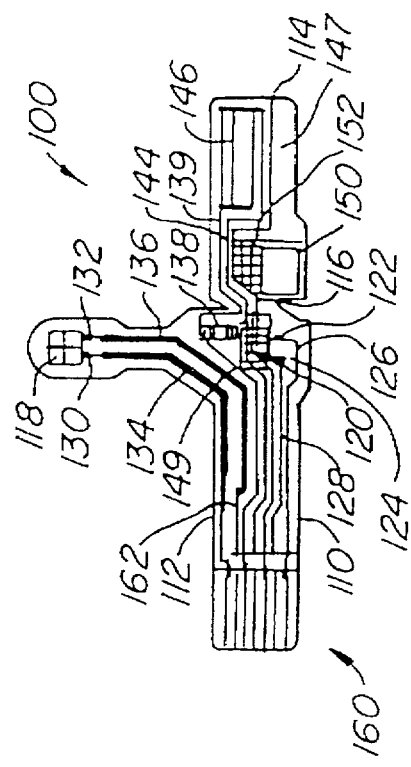
FIG. 6 is a view of the front of the substrate of a sensor according to an alternative embodiment.

FIG. 6 is an elevational view of the front, and FIG. 7 is an elevational view of the back, of an alternate embodiment of the present invention for a neo-natal sensor 100. Substrate 110 is divided into two portions by a hinge area 116: an L-shaped portion 112 and a cover portion 114. A second portion of the substrate 114 folds over a first portion 112. A photoemitter 118 and a photodetector 120 (shown in phantom in FIG. 6) are mounted on substrate portion 112 in the same manner as in the previous embodiment. The leads of photodetector 120 are bonded to conductive traces 126 and 128 at points 122 and 124, respectively. The leads of photoemitter 118 are bonded to traces 134 and 136 at points 130 and 132, respectively. Epoxy is placed over both sets of leads, and the entire circuit is covered with a dielectric coating.

A coding resistor 138 is connected between trace 139 and trace 144. Alternatively, a printed resistor may be formed in area 146.

Conductive coating areas 147 and 149 are provided on the front of substrate 110 and conductive coating area 148 is provided on the back for shielding. Areas 147, 148 and 149 are connected to a ground signal via trace 162. Additional shielding is provided with a thin copper plate 150 having a Faraday shield portion 152 covering hole 166. Plate 150 is bonded to conductive area 147 in the same manner as the optical components and discrete resistor.

Traces 126, 128, 134, 136, 139, 142 and 162 extend into a connector area 160 of substrate 110. Substrate 110 is folded about hinge 116 so that hole 166 leaves photodetector 120 exposed through Faraday shield 152. A connector plug is attached to substrate 110 for connection to a cable connector as in the earlier version. The folded substrate is attached to an adhesive bandage similar in shape and function to the bandage used in the Nellcor Incorporated OXISENSOR N-25 product.

Figure 8:
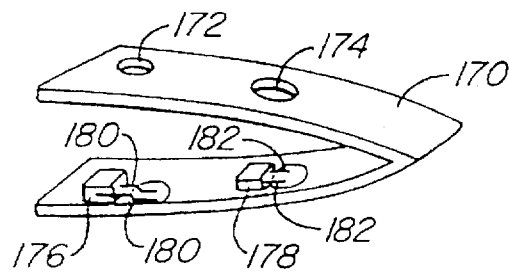
FIG. 8 is a perspective view of an embodiment of the invention using encapsulated die for the emitter and detector.

FIG. 8 illustrates one embodiment in which a strip 170 has openings 172 and 174 on a first portion, while it has a photoemitter 176 and a photodetector 178 on a second portion. In this embodiment, photoemitter 176 is a semiconductor photoemitter die encapsulated in a package with leads 180 extending out of it. These leads 180 are bonded to the traces on strip 170. There are similar leads 182 connecting to the package holding the semiconductor detector 178.

Figure 9:
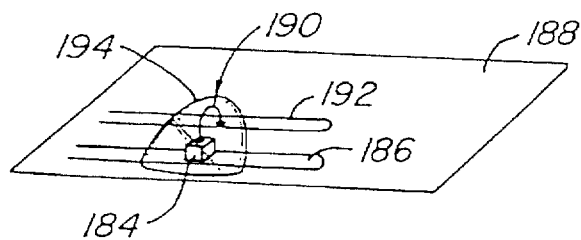
FIG. 9 is a diagram of the use of a non-encapsulated die directly mounted on the strip.

FIG. 9 illustrates an alternate embodiment in which a semiconductor die 184 is mounted directly on a conductive trace 186 on the polyester strip 188. A wire bond 190 is used to connect another portion of die 184 to a second conductive trace 192. The assembled semiconductor die on the strip can be encapsulated with resin 194. This eliminates the need to use a pre-encapsulated chip, giving a more compact structure. Preferably, the semiconductor die will have a contact portion on its bottom surface which is epoxied with a conductive epoxy to conductive trace 186.

Figure 10:
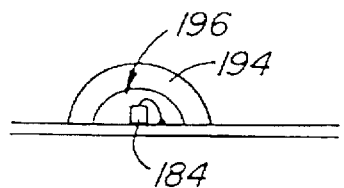
FIG. 10 is a diagram of a lens mounted over the die of FIG. 9.

The clear epoxy overcoat 194 may act as a lens to focus light on the die 184 if the die is a photodetector. Alternately, it may be used as a lens to direct light from a photoemitter or LED. If a specific lens design is preferred, a pre-formed lens 194 may be used as shown in FIG. 10. The gap 196 between the inside of the lens and the die 184 may be filled with a clear epoxy, or may be simply left hollow.

The method for assembling a strip as shown in FIGS. 9 and 10 consist of the following steps. First, the conductive epoxy is silk-screened down on the conductive traces on the flexible strip. Next, the semiconductor dies are placed on the conductive epoxy for contact with the back of the dies. The epoxy is then cured to form the connection. A wire bond is then attached to the top of the chip, and thereafter to a pad on the second conductive trace. If necessary, conductive epoxy can be placed on a second conductive trace and the gold wire bond can simply be buried or pushed into the epoxy prior to curing. Last, a clear epoxy overcoat is applied over the chip and the wire bond. In addition, the pre-molded lens may be placed on top. Preferably, both the clear epoxy and the conductive epoxies are cured at the same time.

Figure 11:
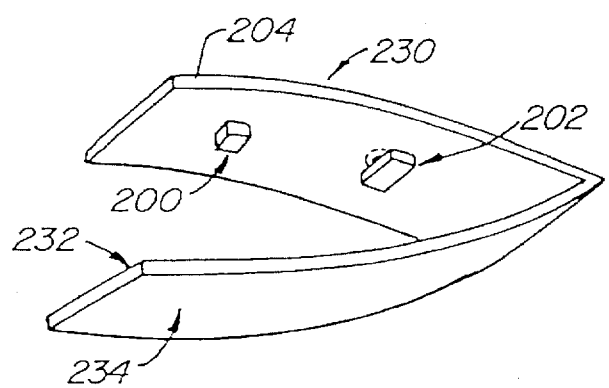
FIG. 11 is a diagram of an embodiment in which the emitter and detector are mounted over the openings on the strip.
Figure 12:
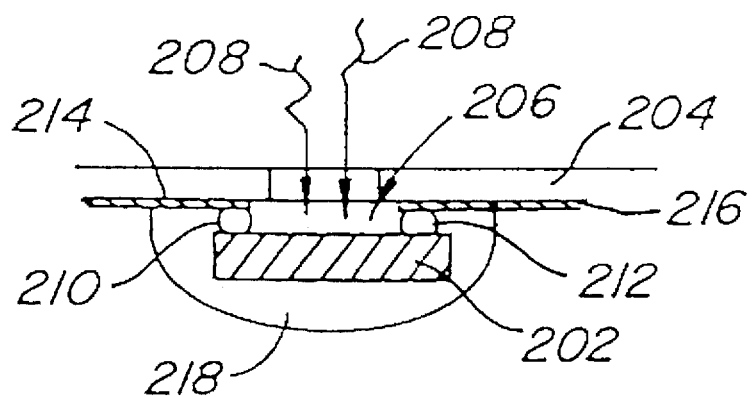
FIG. 12 is a diagram illustrating the bonding of the die of FIG. 11 in more detail.

FIG. 11 illustrates an alternate embodiment in which semiconductor dies or chips are used which have contacts on the same side as the LED and/or detector. As shown in FIG. 11, a light emitter 200 and a detector 202 are mounted over openings on a polyester strip 204. This is illustrated in more detail in FIG. 12, where detector 202 is shown mounted over an opening 206 in strip 204. Detector 202 receives light indicated by lines 208 on a surface which is photosensitive. On the same side of the die or chip, contacts 210 and 212 are connected to conductive traces 214 and 216, respectively.

In one embodiment, detector 202 is a semiconductor die with contact regions on either end which are epoxied to the conductive traces. In another embodiment, the photodetector may be a packaged photodetector in a surface-mount package having contacts on the bottom or side, rather than leads extending from a lead frame encapsulated in the package. Again, an overcoat of epoxy 218 may be applied to protect the die and leads. In one embodiment, contacts 210 and 212 are conductive epoxy.

Figure 13:
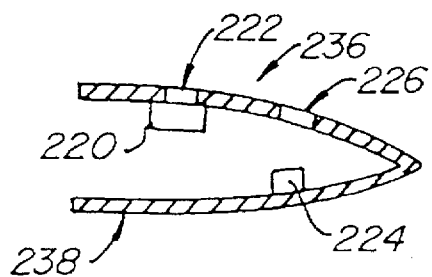
FIG. 13 is a diagram of an embodiment, the emitter and the detector on opposite portions of the folded strip.
Figure 14:
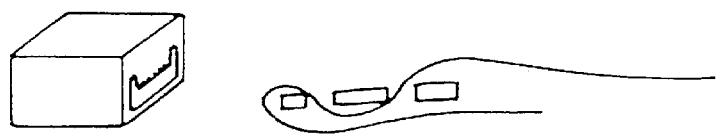
FIG. 14 is a diagram illustrating a first technique for attaching the strip to a tab with two slots.
Figure 15:
FIG. 15 is a diagram of a second technique for attaching the strip to a tab using two slots.
Figure 16:
FIG. 16 is a diagram of a technique for attaching the strip to a tab having a single slot.
Figure 17:
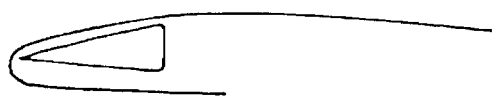
FIG. 17 is an illustration of a slotless wedge for attaching the tab to the connector.

FIG. 13 illustrates an alternate embodiment combining aspects of different embodiments with the photodetector 220 mounted directly over opening 222, while photoemitter 224 is opposite a hole 226. Alternately, the photoemitter and photodetector may be reversed.

Other combinations of the above embodiments are possible. If a clear flexible substrate is used, holes for light transmission are not necessary. If opaque substrates are used, holes are required or a clear portion of the substrate is required for the LED or detector. Alternately, the detector or emitter could be mounted on the outside of the substrate, and covered with the epoxy to protect it and allow direct contact with a patient's skin. Where holes are used, the LED or detector should be covered with a protective layer as a passivation layer to prevent electrical contact with the patient's skin.

The above embodiments allow for various placements of the conductive shielding referred to above. For instance, an embodiment of FIG. 11, conductive shielding can be applied to a side 230 of strip 204 opposite devices 200 and 202. On the other portion of the folded strip, the conductive shielding may be either applied to an inside surface 232, or, alternately, to an outside surface 234. In the embodiment of FIG. 13, the conductive shielding is preferably applied to the outside surfaces 236 and 238, respectively.

As will be understood by those familiar with the art, the present invention may be embodied in other specific forms without departing from the spirit or essential characteristics thereof. Accordingly, the disclosure of the preferred embodiment of the invention is intended to be illustrative, but not limiting, of the scope of the invention which is set forth in the following claims.

What is claimed is:

1. A non-invasive, electrooptical sensor for removable attachment to the skin of a patient comprising:

a first flexible substrate having first and second portions which are connected to each other;

a light emitter mounted on one of said first and second portions of said first substrate;

a light detector mounted on one of said first and second portions of said first substrate;

a plurality of conductive lines deposited on said first substrate, at least one being connected to said light emitter and at least one being connected to said light detector, at least two of said conductive lines extending across a first surface of said first portion and a second surface of said second portion, said first and second surfaces facing each other, said light emitter and light detector facing the same direction;

an insulating layer separating said first and second surfaces; and wherein at least one of said light emitter and light detector comprised an unpackaged semiconductor die having an electrical contact pad on a face thereof, which is directly mounted on a conductive area on said flexible substrate and electrically connected thereto.

2. The sensor of claim 1 further comprising a wire bond coupling an electrical contact pad on a second face of said semiconductor die directly to another conductive area on said substrate.

3. The sensor of claim 1 wherein the semiconductor face has a second electrical contact pad thereon which is directly mounted on a second conductive area on said flexible substrate and electrically connected thereto.

4. The sensor of claim 1 further comprising a coding resistor on the substrate whose value is trimmed to provide an indication of a wavelength of the light emitter after the light emitter is mounted on the substrate.

5. The sensor of claim 1 further comprising:

a pre-formed lens covering said unpackaged semiconductor die.

6. The sensor of claim 5 further comprising a clear epoxy covering and encapsulating said semiconductor die, between said semiconductor die and said lens.

7. The sensor of claim 1 further comprising:

a Faraday shield on said first substrate adjacent said light detector.

* * * * *